United States Patent [19]

Thornton-Trump

[11] 4,275,593
[45] Jun. 30, 1981

[54] SPECIFIC GRAVITY METER FOR AIRCRAFT DE-ICING EQUIPMENT

[76] Inventor: Walter E. Thornton-Trump, 108 Bellvue Dr., Beaver Lake, Plattsmouth, Nebr. 68048

[21] Appl. No.: 27,924

[22] Filed: Apr. 6, 1979

[51] Int. Cl.³ .............................................. G01N 9/16
[52] U.S. Cl. ..................................................... 73/454
[58] Field of Search ...................... 73/454; 244/134 C; 134/111, 123; 137/91

[56] References Cited

U.S. PATENT DOCUMENTS

| | | | |
|---|---|---|---|
| 288,402 | 11/1883 | Borodoulin | 73/454 |
| 2,445,255 | 7/1948 | Younkin | 137/91 |
| 3,612,075 | 11/1971 | Cook | 244/134 C |

*Primary Examiner*—S. Clement Swisher

*Attorney, Agent, or Firm*—Fitch, Even, Tabin, Flannery & Welsh

[57] ABSTRACT

Apparatus is disclosed for determining the proportion of ethylene glycol in an aqueous solution that is used to remove as well as prevent the accumulation of ice and snow on commercial aircraft, the apparatus being used in de-icing equipment of the type which has a self-propelled vehicle, a large capacity heater which heats water carried on the vehicle, a proportioning system for mixing the water and ethylene glycol and pumping means for pumping the solution containing the desired proportion of ethylene glycol under high pressure through a nozzle which is directed toward the aircraft. The apparatus can determine the percentage of ethylene glycol that is contained in the aqueous solution at any time during the operation of the de-icing equipment.

13 Claims, 4 Drawing Figures

SPECIFIC GRAVITY METER FOR AIRCRAFT DE-ICING EQUIPMENT

The present invention generally relates to aircraft de-icing equipment and, more specifically, to apparatus for determining the concentration of ethylene glycol in an aqueous solution that is being used to either remove ice and snow from the surface of an aircraft or to coat the surface with a solution to prevent the formation of ice or the accumulation of ice and snow on the aircraft surfaces.

A method for de-icing aircraft which has ice or snow on its outer surface is comprehensively set forth in my U.S. Pat. No. 4,032,090, and generally involves heating an aqueous solution that is substantially free of glycol to a high temperature, i.e., on the order of 160° to 190° F., and then directing the heated water in a concentrated stream onto the aircraft skin in a manner whereby the heated water will loosen the ice and snow and wash it from the surface. The excess water then falls from the aircraft and is drained away. Under certain atmospheric conditions, the heated water forms a film on the skin and warms the skin to prevent additional ice from forming thereon, and under other atmospheric conditions, the heated water film will evaporate from the skin, thereby chilling it and drying it so as to minimize sticking of blowing snow on the skin. After the ice and snow have been substantially removed, an anti-icing step is often performed which is accomplished by spraying a foglike spray to provide a thin dust coat using an anti-icing solution that substantially comprises water and a predetermined low percentage of ehtylene glycol, i.e., on the order of about 30%, in sufficient quantity that run-off of the solution is minimized.

While the foregoing generally describes the method of de-icing commercial aircraft, reference should be made to the above-referenced patent for a comprehensive description of the details of the method, particularly with respect to particular steps and considerations involved with respect to its use under specific atmospheric conditions. The method can be carried out using de-icing equipment, such as Model No. D40D manufactured by Trump, Inc. of Plattsmouth, Nebr, or with a conversion unit for older de-icing machines, the latter of which is described in my U.S. Pat. No. 4,073,437. The Model D40D aircraft de-icer is a totally self-contained unit which generally comprises a self-propelled vehicle which can be driven near the aircraft, and which has a large boom with a basket at the end thereof in which an operator can stand and spray the aircraft using a hand-held nozzle. The de-icer has a reservoir for water as well as one for ethylene glycol and contains pumping equipment for pumping the solution through conduits to the nozzle, proportioning equipment for varying the proportion of ethylene glycol that is mixed with the water to obtain the desired de-icing solution, and a high capacity heater for heating the solution that is to be pumped through the nozzle.

As is apparent from the broad description of the method that has been described herein, the proportion of ethylene glycol in the de-icing solution will change depending on whether a de-icing step is being carried out or whether an anti-icing step is being done after the ice has been removed from the aircraft. As previously mentioned, when ice and snow is initially being removed from the aircraft, i.e., the de-icing step, the solution is substantially free of ethylene glycol, essentially comprising heated water. However, after the snow and ice have been removed, the dust coat may be applied to the surface which has an increased proportion of ethylene glycol in the solution and is preferably on the order of about 30% ethylene glycol.

The operator in the basket of the aircraft de-icer has a proportioning valve which permits him to vary the proportion of ethylene glycol that is being added to the water that is being pumped through the nozzle and the lever is positioned adjacent a suitably calibrated gauge and thereby provides an indication of the proportion of ethylene glycol resulting de-icing solution. However, the proportioning lever actually only determines the amount of solution from one tank or reservoir on the aircraft de-icer that is being mixed with the fluid from the other reservoir containing the water. Presumably, the reservoir containing the ethylene glycol is 100% ethylene glycol, but operator error in filling the ethylene glycol reservoir with less than 100% solution would result in an actual proportion less than that shown by the proportioning equipment lever and gauge. Since there is the possibility that this could occur, the proportioning equipment is not 100% reliable in determining the actual concentration of ethylene glycol in the solution that actually is pumped through the nozzle onto the aircraft. Since commercial aircraft pilots and ground support personnel are obviously concerned about the possibility of water being sprayed on the aircraft turning to ice, they have often questioned the actual content of the de-icing solution that is being used and for this reason have had considerable misgivings about the use of the method in its preferred embodiment.

Because of their desire to know exactly what concentration of ethylene glycol is being pumped through the nozzle at a particular time, efforts have been made to actually measure the volumetric flow of fluid from the ethylene glycol reservoir as well as the flow of water from the water reservoir and perform a computation of the percentage of ethylene glycol that is present in the solution that is being pumped through the nozzle and provide an electronic digital read-out of the same. This system is extremely expensive and suffers from the basic deficiency of assuming that the tank or reservoir containing the ethylene glycol is 100% ethylene glycol. Obviously, if the ethylene glycol tank had an actual concentration of 50% ethylene glycol as opposed to 100%, then the digital read-out would be twice as high as what is actually being pumped through the nozzle.

Accordingly, it is an object of the present invention to provide an improved apparatus that can be used with an aircraft de-icing unit of the foregoing type which will accurately measure the actual proportion of ethylene glycol that is present in the water solution that is being pumped through the nozzle and do so in an efficient reliable manner.

Another object of the present invention is to provide an improved apparatus that will provide a measurement of the actual proportion of ethylene glycol in a water solution, which operates efficiently and reliably and which is inexpensive in terms of construction and maintenance costs.

Still another object of the present invention is to provide an improved apparatus of the foregoing type which can be almost continuous in its operation so that an operator can continuously monitor the proportion of ethylene glycol in the solution that is being sprayed onto the aircraft and thus be confident that the desired proportional solution is being used.

Still other objects and advantages will become apparent upon reading the following detailed description, in conjunction with the attached drawings, in which.

Figure 1:
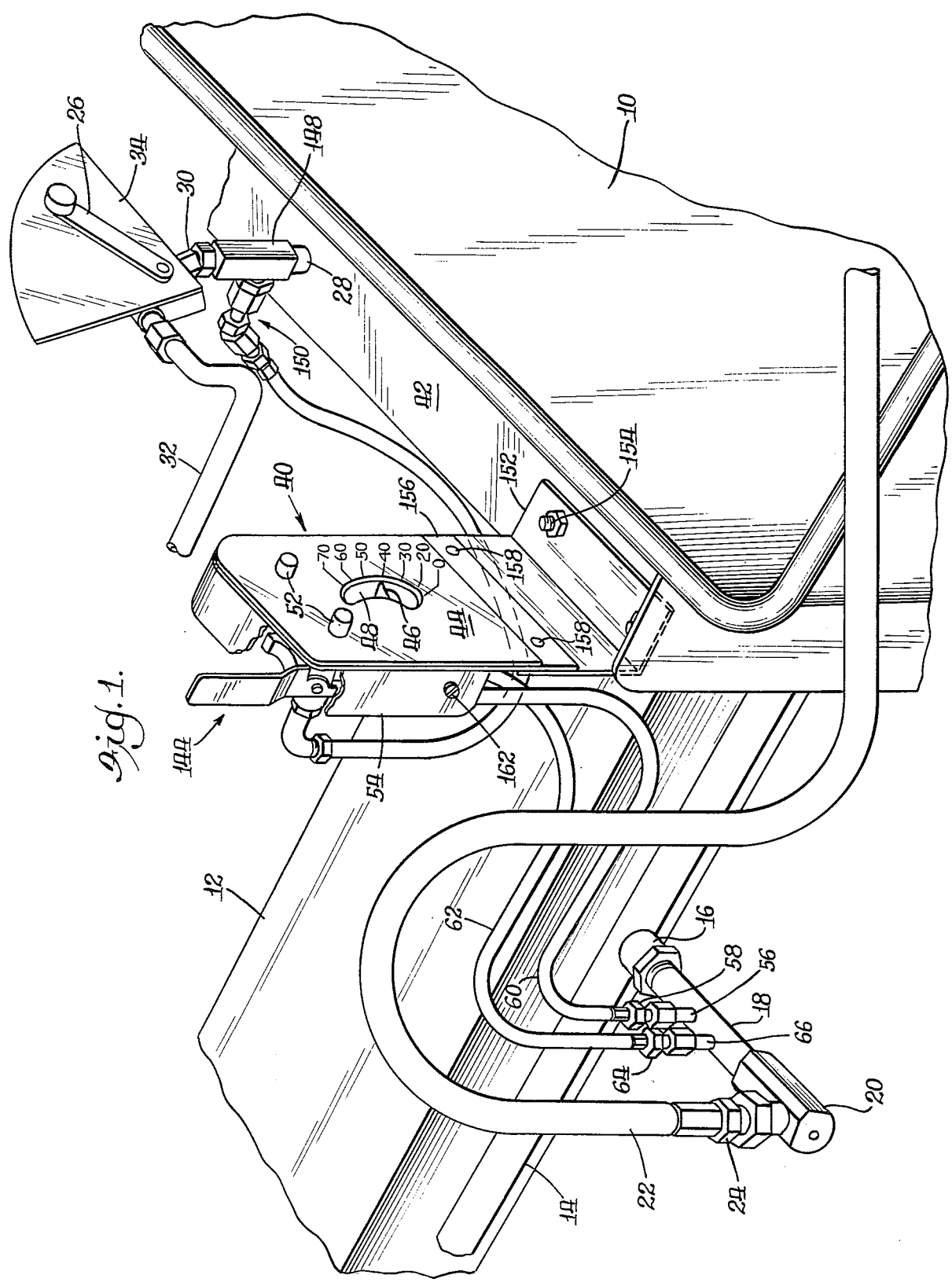
FIG. 1 is a perspective view of apparatus embodying the present invention shown together with a portion of an aircraft de-icer unit.

Turning now to the drawings, and particularly FIG. 1, an embodiment of the apparatus invention is shown together with a portion of an aircraft de-icer unit, particularly illustrating a basket 10 that is located at the end of a boom, indicated generally at 12, which extends from the vehicle containing the reservoirs for the water as well as the ethylene glycol, the pumping equipment, the heating equipment, as well as other components of the unit. The de-icing solution that is pumped through the nozzle comes through a conduit 14 that is attached to the boom 12 with the solution traveling through an angled fitting 16, a short length of conduit 18 to another angle fitting 20 where it is connected to a flexible tubing 22 which is connected to the fitting 20 by a suitable connector 24. Tubing 22 extends to a nozzle (not shown) for spraying of the aircraft that is to be de-iced. The solution in the conduit 14 contains whatever proportion of ethylene glycol that has been added by virtue of a proportioning system that is located upstream of the conduit 14. As previously mentioned, the operator in the basket 10 can vary the proportion of ethylene glycol that is to be mixed in the solution, and does so by manipulating a proportioning lever 26 that controls the flow of glycol through a conduit 28 that extends from the ethylene glycol reservoir to a proportioning valve 30 that is controlled by the lever 26. A conduit 32 is also connected to the outlet of the proportioning valve 30 and extends back to a suitable fitting connected to the conduit 14 so that by manipulating the lever 26, a greater or lesser flow of ethylene glycol can be fed into the conduit 14 to vary the proportion thereof as is desired. While the lever 26 also functions as an indicator in that its position relative to the markings on a flat plate 34 is visible to the operator, the apparatus of the present invention is adapted to provide an accurate indication of the proportion of ethylene glycol that is actually present in the solution that is being pumped through the conduit 14.

The apparatus embodying the present invention, indicated generally at 40, provides a reading of the proportion of ethylene glycol that is present in the solution being pumped, with the apparatus 40 being attached to a shelf 42 that contains the controls for the boom as well as the proportioning lever as previously described. The apparatus has a front face 44 upon which graduations of ethylene glycol in terms of percentages are shown with a pointer 46 being visible through a sight glass 48 that is exposed through an opening 50 in the front face panel 44. A pair of indicating lights 52 are provided to illumninate the front face so that an operator can read the position of the pointer 46 during nighttime. The apparatus has a metal enclosure 54 for enclosing the components to protect them and the enclosure 54 has suitable openings (not shown) through which tubes may enter.

Broadly stated, the apparatus of the present invention effectively samples the fluid from the conduit 18 by having a tube 56 inserted into the interior of the conduit 18 and oriented in the upstream direction, i.e., to the right as shown in FIG. 1, so that fluid flowing through the conduits 14 and 18 is forced into the tube 56 and through a connector 58 into a flexible tubing 60 that extends to a reservoir in the apparatus 40 and a similar return tube 62 extends from the apparatus 40 to a connector 64 which is attached to another tube 66 that also extends into the interior of the conduit 18 and is bent so as to be directed downstream or to the left as shown in FIG. 1 for returning the liquid to the conduit. Thus, during flow of the solution through the conduit 18, fluid is circulated into and out of the reservoir of the apparatus 40 and so as to provide a generally continuous sample that accurately reflects the concentration of ethylene glycol in the solution that is being pumped out of the nozzle.

Within the reservoir of the apparatus 40 is the pointer 46 which pivots around a fixed axis. The position or elevation of the pointer is a function of the specific gravity of the liquid in the reservoir and this is accurately calibrated to provide a reading of the percentage of ethylene glycol in the solution. Thus, on the face plate 44, in the event the pointer is pointed to the line identified as 30, this is an indication that the solution present in the reservoir contains 30% ethylene glycol. If the percentage of ethylene glycol increases in response to manipulation of the lever 26, the pointer 46 will rise and reach an elevation that can be easily read by the operator. As will be more fully explained hereinafter, the tubing, connectors and other components in which the fluid passes must be sufficiently strong to withstand the relatively high operating pressures that are achieved during operation, since the de-icing solution is pumped from the nozzle in substantial quantity and must travel significant distances to reach the surfaces of the aircraft, particularly when the aircraft being de-iced is a jumbo commercial aircraft. In this regard, the operating pressures are often on the order of 350 p.s.i., which means that the components, tubing and the like must be sufficiently strong to withstand pressures of this magnitude.

Figure 4:
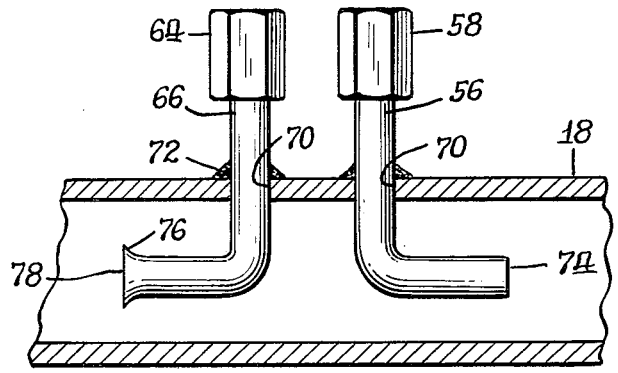
FIG. 4 is a side view with portions removed, illustrating the parts of the apparatus which remove and return the solution that is measured.

With respect to the details of the tubes 56 and 66 that are inserted into the conduit 18, reference is made to FIG. 4 which shows a side elevation of the same with portions removed and the tubes 56 and 66 are inserted through suitable apertures 70 located in the conduit 18 and are welded by weldments 72 as shown. While both of the ice tubes have essentially 90° angles therein as shown, the upstream directed tube 56 has an end 74 that is of the same diameter as the remainder of the tube 56. However, with respect to the downstream directed tube 66, it has an outwardly flanged end portion 76 which creates a reduced pressure at the opening 78 which will aid in increasing the flow of fluid through the apparatus 40 to insure the rapid exchange of solution so that the solution contained within the reservoir of the apparatus 40 accurately represents the fluid that is being pumped through the nozzle at any particular time.

Figure 2:
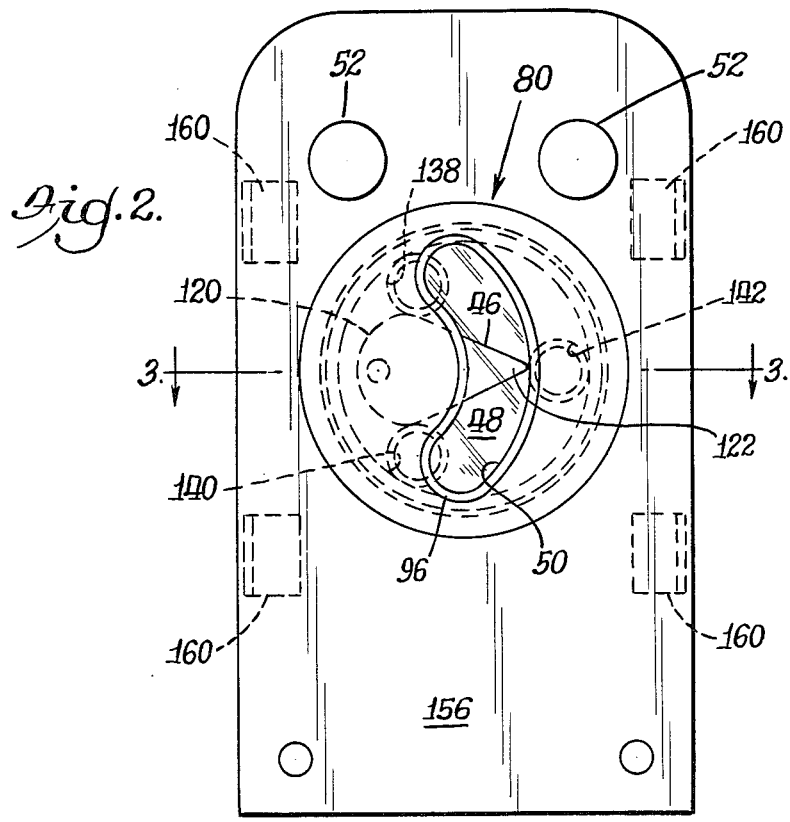
FIG. 2 is a front view of a portion of the apparatus embodying the present invention which is shown in FIG. 1.
Figure 3:
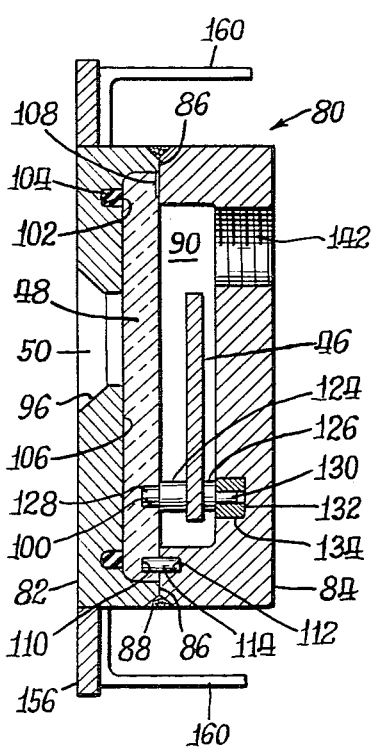
FIG. 3 is a cross-section of the apparatus shown in FIG. 2.

Turning now to the detailed construction of the apparatus 40 and referring to FIGS. 2 and 3, it comprises a housing, indicated generally at 80, which is cylindrical in shape and is comprised of two mating sections 82 and 84 which are connected together along an interface defined by line 86 by a weldment 88 located within beveled portions as shown. The weldment 88 extends around the complete circumference of the beveled portion and is preferably ground so as to present a smooth outer surface as shown. A reservoir 90 is contained within the housing 80 and is formed by cutting the material from a solid stock of cylindrical metal, preferably steel or the like. A cylindrical portion cut from the section 82 is slightly larger than the cylindrical portion cut from the section 84, but both cuts define the reservoir 90 in which the pointer 46 is located. The section 82 also has the generally crescent-shaped opening 50 therein with a beveled surface 96 extending completely around the opening 50 which aids an operator in viewing the pointer. The portion cut away from the section 82 contains a sight glass 48 that is circularly shaped and of sufficient thickness to withstand the high fluid pressures that are experienced, and the thickness is preferably about ¼ inch. It is preferred that the sight glass 48 be fabricated from plexiglass which can be relatively easily cut and because it contains a circular recess 100 into which a trunnion of the pointer 46 is pivotally positioned. The section 82 also has an annular groove 102 in which an annular O-ring 104 is located for providing a seal between the plexiglass sight glass 48 and an interior face 106 of the cylindrical recess. Additionally, a gasket 108 is provided between the sight glass 48 and the section 84 along the interface line 86 to compensate for minor variations in the thickness of the plexiglass 48 that may be present. The annular seal 108, together with the O-ring 104, thereby insure a tight seal and prevent any liquid in the reservoir 90 from leaking around the outside of the sight glass 48 and out of the opening 50. Since the sight glass has the cylindrical recess 100 therein for receiving the pointer, it is important that the circular sight glass be accurately positioned within the cylindrical recess 106 and to this end, a second aperture 110 is located within the sight glass with a cooperating aperture 112 being located in the section 84 so that a positioning pin 114 can be provided to accurately align the sight glass within the recess 106.

The pointer 46 generally comprises a semi-circular portion 120 near the end containing the pivot, with the opposite end extending to a point 122 as shown in FIG. 2. The pointer 46 is generally flat and has a pair of trunnions 124 and 126 on opposite sides, with the trunnions having a reduced diameter outer portion 128 and 130, respectively, for engagement with the opening 100 in the sight glass 48 and with a bushing 132 located in a larger cylindrical recess 134 of the section 84 of the housing 80. The bushing 134 is preferably fabricated from Delrin plastic made by the DuPont Company in Wilmington, Del., to insure relatively low friction that could restrict the movement of the pointer during operation and to minimize wear between the trunnion 130 and the bushing itself. The pointer 46 is made of a plastic material and is preferably substantially identical to the pointer construction that is utilized in the Model No. 700-1125 specific gravity meter maufactured by The Ballkamp Corp. of Indianapolis, Ind. The pointer contained in the aforementioned meter is temperature compensated so as to provide an accurate reading within the range of temperatures contemplated when using the method described in my aforementioned U.S. Pat. No. 4,073,437.

The housing section 84 is provided with three threaded tapped openings 138, 140 and 142, with the opening 138 being adapted to receive the tubing 60 which communicates the solution to the reservoir 90 through a suitable fitting (not shown) and the opening 140 is connected to the tubing 62 through a suitable fitting (not shown) that communicates the solution back into the conduit 18 during operation. The opening 142 receives the fitting associated with a valve 144 which in turn is connected to a tubing 146 that extends to a T-fitting 148 that is located in the ethylene glycol conduit 28 and is suitably connected thereto by fittings indicated generally at 150. The valve 144 is used to purge the apparatus 40 to insert substantially 100% ethylene glycol within the reservoir 90 when the de-icing equipment is not being used, so that freezing temperatures will not cause water to freeze and damage the apparatus of the present invention.

The apparatus 40 is mounted on the shelf 42 by a right angled mounting bracket 152 that is bolted to the shelf by bolts 154 and to a plate 156 by bolts 158. As is best shown in FIG. 3, the plate 156 is suitably welded to the housing section 82 in a manner whereby it is substantially flush with the leftward surface thereof and the plate 156 has right angled brackets 160 connected thereto by welding or the like which provide supports to which the outer enclosure 56 can be attached by screws 162 as shown in FIG. 1.

During operation, it is preferred that the nozzle be shut-off so that flow is stopped in the conduits 14 and 18 while the apparatus 40 is being read, to eliminate any disturbance to the pointer 46 which may be caused by the turbulent action of the solution flowing through the reservoir 90. It is also important for the reason that with the nozzle on, the operator who is attempting to read the concentration of the ethylene glycol is viewing the pointer rather than directing his attention to where the nozzle is spraying and if the nozzle is kept on, ground personnel or equipment may be inadvertently sprayed with the de-icing solution. Thus, it is preferred that the nozzle be shut-off when the indicator is being read and the most accurate reading will be obtained when this is done, since solution will not be flowing through the reservoir 90 during this time.

From the foregoing description, it should be appreciated that a novel apparatus for precisely determining an actual percentage of ethylene glycol that is being pumped through the nozzle has been described which has many advantages and desirable attributes. The apparatus is relatively inexpensive to manufacture and can be retrofitted into existing de-icing equipment as well as easily provided on new equipment. The desirability of having accurate reliable information concerning the content of the solution that is being sprayed onto aircraft is readily apparent, particularly when considering the value of the aircraft that is receiving the de-icing and anti-icing treatment.

It should be understood that while a preferred embodiment of the present invention has been described herein, various modifications, alternatives and substitutions will become apparent to those skilled in the art, and, accordingly, the scope of the present invention should be defined only by the appended claims and equivalents thereof.

Various features of the present invention are set forth in the following claims.

What is claimed is:

1. Apparatus for use in aircraft de-icing equipment of the type which has means for pumping an aqueous de-icing solution through a nozzle onto an aircraft or the like to remove ice and snow therefrom and to prevent the accumulation thereof on the aircraft, said apparatus providing a measurement of the proportion of ethylene glycol in the aqueous solution that is flowing through the nozzle, and comprising:
- means connected upstream of the nozzle for communicating the solution to and from a reservoir means;
- means defining a reservoir for receiving the solution, the reservoir means having a transparent face portion through which indicator means can be viewed;
- pointer means pivotally mounted within said reservoir means and being adapted to reach a vertical position that varies in direct proportion to the amount of ethylene glycol that is present in the solution; and,
- indicating means adjacent said pointer means for providing accurate graduated increments of the proportion of ethylene glycol in the solution and thereby enable an observer to view the pointer means and indicating means and obtain an accurate measurement of the proportion of ethylene glycol in the solution.

2. Apparatus as defined in claim 1 further including means for purging said reservoir to substantially increase the proportion of ethylene glycol therein when said de-icing equipment is not in use.

3. Apparatus as defined in claim 1 wherein said communication means comprises a tube inserted within the line carrying the aqueous de-icing solution to the nozzle, said tube having an opening directed upstream so that flow of said solution will directly enter said tube, said tube being connected to conduit means that is in turn connected to said reservoir means, said communicating means also including a second tube located downstream of said first tube and being directed in the downstream direction, said tube being directed to a second conduit means which is also connected to said reservoir means, said communicating means being effective to provide a flow of de-icing solution through the first conduit means, the reservoir and the second conduit means when said solution is flowing through the nozzle.

4. Apparatus as defined in claim 3 wherein said second tube has an outwardly flared end.

5. Apparatus as defined in claim 1 wherein said reservoir means comprises two sections, each section having a recess therein, the recess of said second section being larger than said first and carrying a transparent plate therein, said second section having an opening adjacent the transparent plate, said reservoir means including means for attaching said sections together.

6. Apparatus as defined in claim 5 including sealing means located between said opening and said transparent plate.

7. Apparatus as defined in claim 6 wherein each of said recesses and said transparent plate are substantially cylindrical, the inside diameter of the recess of said second plate being less than the inside diameter of said first section, an annular surface of said first section being urged against said transparent plate to hold said plate firmly against said sealing means.

8. Apparatus as defined in claim 7 wherein said sealing means comprises an O-ring seal.

9. Apparatus as defined in claim 7 further includng gasket means located between said transparent plate and said annular surface of said first section.

10. Apparatus as defined in claim 7 wherein said means for attaching said first and second sections together comprise a weldment.

11. Apparatus as defined in claim 5 wherein said transparent plate is plexiglass.

12. Apparatus as defined in claim 11 wherein each of said transparent plate and said first section have apertures therein for receiving trunnions located on opposite sides of said pointer means, said pointer means generally comprising a flat plate and having a point on the end opposite the end having said trunnions.

13. Apparatus as defined in claim 2 wherein said purging means includes a conduit extending from the supply of ethylene glycol and a valve operatively located in the conduit for controlling the flow of ethylene glycol into said reservoir.

* * * * *